(12) United States Patent
Higaki et al.

(10) Patent No.: US 6,576,135 B1
(45) Date of Patent: Jun. 10, 2003

(54) METHOD FOR SEPARATING LACTONE-CONTAINING HIGH-MOLECULAR WEIGHT COMPOUNDS

(75) Inventors: Tomoji Higaki, Osaka (JP); Takashi Yoshiyasu, Osaka (JP); Norihiro Hashimoto, Osaka (JP); Keiji Honda, Osaka (JP); Hiroshi Hatanaka, Osaka (JP); Michio Yamashita, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/069,964

(22) PCT Filed: Sep. 5, 2000

(86) PCT No.: PCT/JP00/06023

§ 371 (c)(1),
(2), (4) Date: Mar. 8, 2002

(87) PCT Pub. No.: WO01/18007

PCT Pub. Date: Mar. 15, 2001

(30) Foreign Application Priority Data

Sep. 8, 1999 (JP) ............................................. 11-253813

(51) Int. Cl.$^7$ ................................................ B01D 15/08
(52) U.S. Cl. ...................... 210/635; 210/656; 549/263
(58) Field of Search ................................. 210/635, 656, 210/659, 198.2; 549/263

(56) References Cited

U.S. PATENT DOCUMENTS 5,130,157 A * 7/1992 Hulsker ...................... 549/295

FOREIGN PATENT DOCUMENTS

| EP | 0 382 173 | 8/1990 | .................. 549/263 |
| GB | 2 157 682 | 10/1985 | .................. 549/263 |
| JP | 03 191788 | 8/1991 | .................. 549/263 |

OTHER PUBLICATIONS

H. Oka et al.: "Separation of antibiotics by counter–current chromatography" Journal of Chromatography, A., vol. 812, No. 1–2, pp. 35–52 Jul. 3, 1998.

W. Wang–Fan et al.: "Application of centrifugal counter-current chromatography to the separation of macrolide antibiotic analogues" Journal of Chromatography A., vol. 864, pp. 69–76 1999.

* cited by examiner

Primary Examiner—Ernest G. Therkorn
(74) Attorney, Agent, or Firm—Oblon, Spivak, McClelland, Maier & Neustadt, P.C.

(57) ABSTRACT

A method for separating a lactone-containing high-molecular weight compound comprising subjecting a mixture of a lactone-containing high-molecular weight compound having, as its side-chain, at least one of a lower alkenyl group and a lower alkoxy group and its analogous compound(s) to either one or both steps in any order of a step (A) for adsorbing the mixture to a nonionic adsorption resin and eluting with an aqueous solvent containing silver ions, and a step (B) for adsorbing the mixture to a basic active alumina and eluting with an organic solvent to separate each of the compounds.

13 Claims, 1 Drawing Sheet

METHOD FOR SEPARATING LACTONE-CONTAINING HIGH-MOLECULAR WEIGHT COMPOUNDS

TECHNICAL FIELD

The present invention relates to a method for separating analogous lactone-containing high-molecular weight compounds, more particularly a method for separating lactone-containing high-molecular weight compounds having different side-chains by using a nonionic adsorption resin and/or a basic active alumina

BACKGROUND ART

It has been known to use silver ions for separating cis-trans isomers of an unsaturated aliphatic acid having the same number of carbon atoms (*J. Chromatography*, 149 (1978) 417-). However, it has been difficult to separate analogous compounds which are slightly and partially different in their molecular structure by usual processes, because they have the same or almost the same number of carbon atoms and accordingly are similar to each other in physical properties such as solubility in and affinity to solvents.

DISCLOSURE OF INVENTION

The inventors of the present invention have made extensive studies for finding a method for effectively separating analogous compounds resembling each other in physical properties without changing their chemical structure. Unexpectedly, they have found a method for separating lactone-containing high-molecular weight compounds having different side-chain by using a nonionic adsorption resin and an appropriate eluent and/or a basic active alumina and an appropriate eluent.

The present invention provides a method for separating a lactone-containing high-molecular weight compound comprising subjecting a mixture of a lactone-containing high-molecular weight compound having, as its side-chain, at least one of a lower alkenyl group and a lower alkoxy group and its analogous compound(s) to either one or both steps in any order of

- a step (A) for adsorbing the mixture to a nonionic adsorption resin and eluting with an aqueous solvent containing silver ions, and
- a step (B) for adsorbing the mixture to a basic active alumina and eluting with an organic solvent to separate each of the compounds.

Preferably, according to the present invention, both steps (A) and (B) are carried out for separating a lactone-containing high-molecular weight compound having, as its side-chains, both a lower alkenyl group and a lower alkoxy group from its analogous compound(s). Either one of steps (A) and (B) may be conducted first, but usually step (A) may preferably be conducted first.

Step (A) is preferably carried out for separating a lactone-containing high-molecular weight compound having, as its side-chain, a lower alkenyl group from its analogous compound(s).

Step (B) is preferably carried out for separating a lactone-containing high-molecular weight compound having, as its side-chain, a lower alkoxy group from its analogous compound(s).

The lactone-containing high-molecular weight compounds to which the separation method of the present invention can be applied mean those having one or more lactone rings in their molecules and having a molecular weight of about 400 or more. They may have a monocyclic, bicyclic, tricyclic or the like basic ring structure. More preferably, the number of member atoms forming said basic ring structure is 12 or more. Such monocyclic compounds include erythromycins, leucomycins, methymycins and the like. Such tricyclic compounds having a lactone ring include tricyclic compounds as shown in EP0184162; hetero atoms-containing tricyclic compounds as shown in EP0427680, EP0532088 or WO93/04680. And the preferable tricyclic compounds having a lactone ring are 1, 14-dihyroxy-12-[2-(4-hydroxy-cyclohexyl)-1-methylvinyl]-23,25-dimethoxy-13,19,21,27-tetramethyl-11,28-dioxa-4-azatricyclo [22.3.1.0$^{4.9}$]octacos-18-ene-2,3,10,16-tetraone (referred to as "Compound Z" hereinafter)(which is tacrolimus when the 17th position is substituted with allyl group and the 3rd position is substituted with methoxy group, and ascomycin when the 17th position is substituted with ethyl group and the 3rd position is substituted with methoxy group), rapamysins, or the like. Among these compounds, tricyclic compounds are preferable and Compound Z is more preferable.

The lower alkenyl group as the side chain in the lactone-containing high-molecular weight compounds may be straight-chain or branched-chain alkenyl groups having 2–6 carbon atoms such as vinyl, propenyl (allyl or 1-propenyl), butenyl, isobutenyl, pentenyl, hexenyl and the like, among which vinyl and propenyl are preferred.

The lower alkoxy groups as the side chain in the lactone-containing high-molecular weight compounds may be straight-chain or branched-chain alkoxy groups having 1–6 carbon atoms such as methoxy, ethoxy, propoxy, isopropoxy, butoxy, isobutoxy, sec-butoxy, tert-butoxy, pentyloxy, isopentyloxy, hexyloxy and the like, among which preferred are those having 1–4 carbon atoms such as methoxy, ethoxy, propoxy, isopropoxy, butoxy, isobutoxy and the like.

Especially, the lactone-containing high-molecular weight compound to be separated according to the present invention which has at least one of the lower alkenyl group and the lower alkoxy group as the side chain is preferably one containing Compound Z as its basic chemical structure in which the lower alkenyl group is propenyl group and the lower alkoxy group is methoxy group, one containing compound Z as its base chemical structure in which the lower alkenyl group is propenyl group, or one containing Compound Z as its basic chemical structure in which the lower alkoxy group is methoxy group.

Analogous compounds to the lactone-containing high-molecular weight compound to which the separation method of the present invention is applied mean compounds having the same or substantially the same basic chemical structure as the above-described lactone-containing high-molecular weight compound but having different substituent(s) as their side-chain(s). For example, compounds analogous to the one having the lower alkenyl groups as its side chain may be those having the same basic chemical structure but having a lower alkyl group, a lower alkoxy group, a hydroxy group or the like instead of the lower alkenyl group at the same position. Such analogous compounds include those having a basic chemical structure somewhat different in other parts than the above-mentioned substitution position but exhibiting similar properties as a whole.

Particularly prefered compounds analogous to the lactone-containing high-molecular weight compound having a lower alkenyl group as its side-chain may be those having a lower alkyl group instead of the lower alkenyl group, compounds analogous to the one having a lower alkoxy group as its side-chain may be those having a hydroxy group instead of the lower alkoxy group, and compounds analogous to the lactone-containing high-molecular weight compound having a lower alkenyl group and a lower alkoxy group as its different side-chains may be those having a lower alkyl group instead of the lower alkenyl group and/or a hydroxy group instead of the lower alkoxy group.

The lower alkyl group as side-chain in the lactone-containing high-molecular weight compounds may be straight-chain or branched-chain alkyl groups having 1–6 carbon atoms such as methyl, ethyl, propyl, isopropyl, butyl, isobutyl, sec-butyl, tert-butyl, pentyl, isopentyl, hexyl and the like, among which preferred are those having 1–4 carbon atoms such as methyl, ethyl, propyl, isopropyl, butyl, isobutyl and the like.

Adsorption of the mixture containing the lactone-containing high-molecular weight compound having at least one of lower alkenyl group and lower alkoxy group as its side-chain(s) and its analogous compound(s) on the nonionic adsorption resin or the basic active alumina, and elution of the object compound from the adsorbent according to the present invention may be carried out in the following manner.

For example, in the case that a mixture of a lactone-containing high-molecular weight compound having at least one of lower alkenyl group and lower alkoxy group as its side chain and its analogous compound(s) is obtained by fermentation, the way to subject the mixture to the separation method depends on whether these compounds are produced out of bacteria, i.e., extracellularly, or whether they are produced inside bacteria, i.e., intracellularly. If they are extracellularly produced, fermentation liquid mixture is subjected to the separation method of the present invention. If the compounds are intracellularly produced, bacteria is treated with an appropriate solvent and the resultant extract liquid mixture is then subjected to the separation method of the present invention. The fermentation liquid mixture or the extract liquid mixture, as it is or after concentrated, may be poured into a column or the like filled with an adsorbent. Alternatively, the fermentation liquid or the extract liquid may be concentrated to dryness to give a residue and then the residue may be dissolved in an appropriate solvent to give a solution, which is poured into the column or the like.

If a mixture of a lactone-containing high-molecular weight compound having at least one of lower alkenyl group and lower alkoxy group as its side chain and its analogous compound(s) is obtained by synthesis, the reaction liquid or extract liquid, as it is or after concentrated, may be poured into a column or the like filled with an adsorbent. Alternatively, the reaction liquid or the extract liquid may be concentrated to dryness to give a residue and then the residue may be dissolved in an appropriate solvent to give a solution, which is poured into the column or the like.

The lactone-containing high-molecular weight compound having at least one of lower alkenyl group and lower alkoxy group as its side-chain(s) and its analogous compound(s) contained in the mixture are selectively eluted according to their affinity to the adsorbent and the eluent, and a combined eluate containing a desired compound is concentrated to dryness. Thus the desired lactone-containing high-molecular weight compound is separated.

The nonionic adsorption resin used as the adsorbent may be a polyethylene resin having a partial structure represented by the formula:

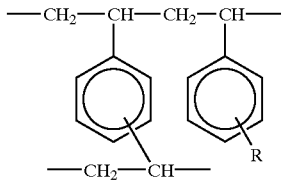

wherein R is a hydrogen or halogen atom. Specifically, preferably used are Diaion® HP 20, Diaion® HP20SS, Sepabeads® SP207 (manufactured by Mitsubishi Chemical Corporation, Japan) or the like. For example, in the case where the basic chemical structure of the lactone-containing high-molecular weight compound is Compound Z, it is usually preferable to use Diaion® HP20SS.

For eluting the lactone-containing high-molecular weight compound adsorbed by the nonionic adsorption resin, a silver ion-containing aqueous solvent is used. As a silver salt contained in the silver ion-containing aqueous solvent, preferred is silver nitrate, silver perchlorate or the like which exists as silver ions in water, among which silver nitrate is preferred in the case where the basic chemical structure of the lactone-containing high-molecular weight compound is Compound Z, for example. The concentration of silver ions varies depending on the nature of the lactone-containing high-molecular weight compound to be separated, but it may be generally 0.059 to 1.18 mol/L, preferably 0.12 to 0.59 mol/L, more preferably 0.18 to 0.47 mol/L, most preferably 0.24 to 0.35 mol/L, in terms of Ag+.

As an aqueous medium for the silver ion-containing aqueous solvent, an aqueous acetone, an aqueous alcohol (e.g., methanol and ethanol), an aqueous acetonitrile or the like may be exemplified. For example, an aqueous acetone may preferably be used in the case where the basic chemical structure of the lactone-containing high-molecular weight compound is Compound Z.

The basic active alumina used as the adsorbent may preferably be AC12 (tradename, manufactured by Sumitomo Chemical Company, Limited, Japan) in the case where the basic chemical structure of the lactone-containing high-molecular weight compound is Compound Z, for example.

An organic solvent is used for eluting the lactone-containing high-molecular weight compound adsorbed by the basic active alumina. The organic solvent used as the eluent may be a conventional one such as ethyl acetate, acetone, dichloromethane, a mixture of chloroform and methanol, a mixture of ethyl acetate and n-hexane or the like. For example, ethyl acetate may preferably be used in the case where the basic chemical structure of the lactone-containing high-molecular weight compound is Compound Z.

The type of the eluent and, if the eluent is a mixed solvent, the mixture ratio thereof are preferably selected according to the nature of the lactone-containing high-molecular weight compound to be separated, through preliminary analysis such as thin layer chromatography (TLC) or the like.

The amount of the adsorbent is preferable 50 times larger than the weight of the lactone-containing high-molecular weight compounds in the case where the adsorbent is a nonionic adsorption resin, and preferably 70 times larger than the weight of the lactone-containing high-molecular weight compounds in the case where the adsorbent is a basic active alumina.

The flow rate SV of the eluting solvent varies depending on the particle size of the adsorbent, and may be usually about 3 to 5 mL/min. in the case of the nonionic adsorption resin and usually about 3 to 5 mL/min. in the case of the basic active alumina.

The fraction(s) containing the lactone-containing high-molecular weight compound having at least one of lower alkenyl group and lower alkoxy group as its side-chain(s) may be detected by an ultraviolet-visible detector or a differential refractive index detector, or by TLC after obtaining several fractions. Fractions containing a desired substance are combined and evaporated to dryness under reduced pressure, whereby the desired substance is purified.

Although the present invention is the separation method for a lactone-containing high-molecular weight compound having at least one of lower alkenyl group and lower alkoxy group as its side-chain(s), it is possible to further separate an analogous compound remaining from the other analogous compounds after the separation of the lactone-containing high-molecular weight compound. For example, a lactone-containing high-molecular weight compound having a lower alkoxy group as its side-chain is separated from a mixture containing the lactone-containing high-molecular weight compound and an analogous compound having substantially the same basic chemical structure and having a hydroxy group as its side-chain, and then, the invention may be applied again for separating the analogous compound by elution using a solvent having a different polarity.

BEST MODE FOR CARRYING OUT THE INVENTION

Figure 1:
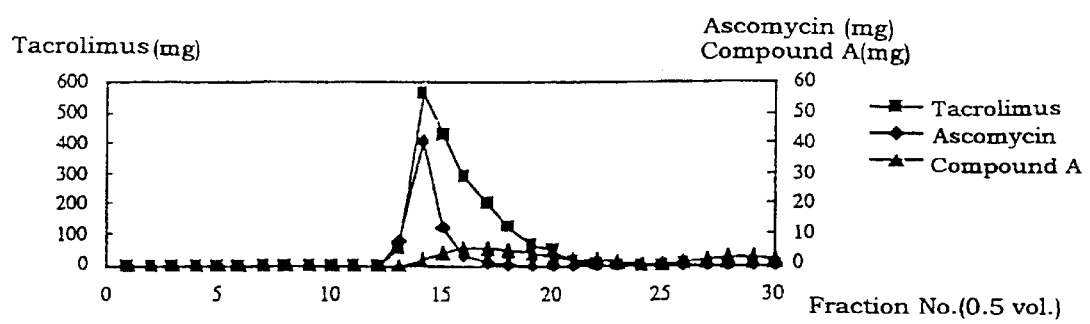
FIG. 1 is a chart showing separation by column chromatography using Diaion® HP20SS and an aqueous acetone as an eluent.

The present invention is now explained in detail by way of examples, which is for illustrating the invention only and should not be construed to limit the scope of the invention.

PREPARATION EXAMPLE 1

Preparation of a mixture containing a lactone-containing high-molecular weight compound having at least one of a lower alkenyl group and a lower alkoxy group as its side-chains and its analogous compound by fermentation A culture medium (100 mL) containing 1% of cornstarch, 1% of glycerin, 0.5% of glucose, 1% of cottonseed meal, 0.5% of dried yeast, 0.5% of corn steep liquor and 0.2% of calcium carbonate was adjusted to pH 6.5, poured into eight 500-mL Erlenmeyer flasks and sterilized at 120° C. for 30 minutes. A loopful of slant culture of Streptomyces tsukubaensis No. 9993 (Deposit No. FERM BP-927 at the National Institute of Bioscience and Human Technology, Agency of Industrial Science and Technology, Japan, under the Budapest Treaty) was inoculated to the medium in each of the flasks and cultured at 30° C. for 72 hours on a rotary shaker. This cultured broth was transferred as a seed culture to 160L of the same medium which was contained in a 200 L jar-fermentor pre-sterilized at 120° C. for 30 minutes and to which 0.05% of Adekanol® (defoaming agent, trademark, manufactured by Asahi Denka Co., Japan) and 0.05% of silicone (manufactured by Shinetsu Chemical Co., Japan) had been added. This was cultured at 30° C. for 48 hours with agitation at 200 rpm under aeration of 160 L/min. This cultured broth (30 L) was inoculated to 3,000 L of a production medium of pH 6.8 pre-sterilized at 120° C. for 30 minutes containing 3% of soluble starch, 0.8% of wheat germ, 0.4% of dried yeast, 0.6% of corn steep liquor, 0.1% of calcium carbonate, 0.05% of Adekanol® and 0.05% of silicone in a 4,000-L tank, and was fermented at 25° C. for 168 hours with agitation at 140 rpm under aeration of 1,500 L/min.

The cultured broth thus obtained was filtered by using 50 kg of diatomaceous earth. Mycelial cakes were extracted with 1,000 L of acetone to give 1,000 L of extract. The acetone extract from the mycelial cakes and the filtrate (2,700 L) were combined to give a crude sample.

EXAMPLE 1

Figure 2:
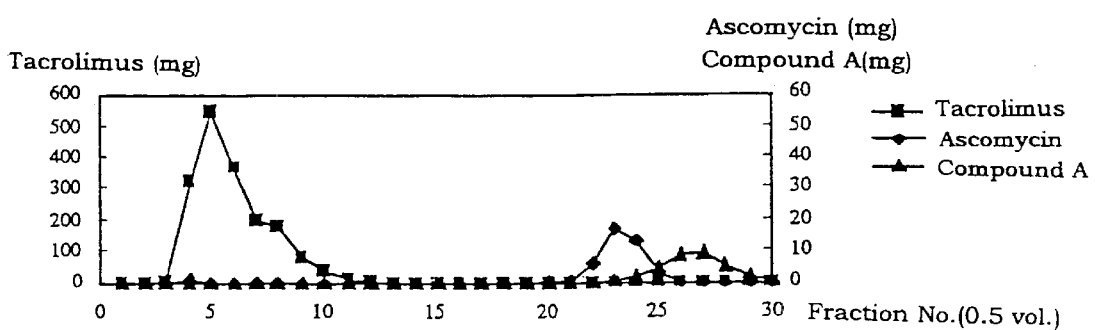
FIG. 2 is a chart showing separation by column chromatography using Diaion® HP20SS and silver nitrate-containing aqueous acetone (0.294 mol/L) as an eluent.

Separation by column chromatography using Diaion® HP20SS as a nonionic adsorption resin and an eluent containing silver nitrate A mixture (200 mg) of tacrolimus, ascomycin and 17-propyl-1,14-dihyroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (referred to as "Compound A" hereinafter) in a 50% aqueous acetone was subjected to column chromatography using Diaion® HP20SS (20 mL) so that substances contained in the mixture were adsorbed. Next, tacrolimus, ascomycin and Compound A were eluted at room temperature by using a 50% (v/v) aqueous acetone containing silver nitrate (0.294 mol/L) and a 60% (v/v) aqueous acetone as eluents at a load of 9.5 g/L-R in terms of tacrolimus. A control test was also carried out in the same manner by using aqueous acetone as an eluent which does not contain silver nitrate. The results are shown in FIG. 1 and FIG. 2.

EXAMPLE 2

Separation by column chromatography using Diaion®& HP20SS as a nonionic adsorption resin and a silver nitrate eluent The crude sample (300 mL) obtained in Preparation Example 1 was subjected to column chromatography using Diaion® HP20SS (20 mL) so that contained substances were adsorbed. The column was washed with 40% aqueous acetone (100 mL). Thereafter, a mixture of tacrolimus and 17-allyl-1,14-dihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (referred to as "Compound B" hereinafter) were eluted at room temperature by using as an eluent a 50% (v/v) aqueous acetone containing silver nitrate (0.294 mol/L). Subsequently, under the same conditions, a mixture of ascomycin and Compound A were eluted separately by using 60% (v/v) aqueous acetone.

The quantity of each compound contained in the separate fractions thus obtained was measured by HPLC analysis (mobile phase: acetonitrile/10% aqueous solution of Polyoxyethylene lauryl alcohol ether (Nakalai Tesque, Inc., Kyoto, Japan)/ water=40/10/50; column: TOSOH TSK-gel ODS-80Tm (5 μm, 4.6φ×150 mm); temperature: 75° C.; wavelength for detection: 210 nm; flow rate: 1.0 mL/min.; injection amount: 20 μL). The results of separation of a mixture of tacrolimus and Compound B, ascomycin and Compound A are shown in Table 1.

TABLE 1

| Fraction No. | Eluent | Distribution of a mixture of tacrolimus and Compound B | Distribution of Ascomycin* | Distribution of Compound A* |
|---|---|---|---|---|
| 0 | Crude sample | 100% | 100% | 100% |
| 1 | Pass liquid | 0% | 0% | 0% |
| 2 | 40% aqueous acetone (washing liquid) | 0% | 0% | 0% |
| 3 | silver nitrate-containing 50% aqueous acetone (0.294 mol/L) | 99.7% | 19.2% | 0% |
| 4 | 60% aqueous acetone (extruding liquid) | 0.3% | 80.8% | 90.7% |
| 5 | 100% acetone (extruding liquid) | 0% | 0% | 9.3% |

*calculated from peak area ratio with respect to tacrolimus

As clearly seen in Table 1, tacrolimus, Compound B, ascomycin and Compound A were not eluted in the pass liquid (fraction 1) or in the washing liquid (fraction 2). They were fully adsorbed by the resin. By elution with the silver nitrate solution (fraction 3), tacrolimus and Compound B were collected approximately 100%, and the elution of Compound A was below a detectable level. In the fraction extruded by the 60% aqueous acetone (fraction 4), ascomycin and Compound A were selectively collected approximately 100%.

To sum up, by adsorbing the mixture of lactone-containing high-molecular weight compounds having a lower alkenyl group as their side-chain (tacrolimus and Compound B) and their analogous compounds (ascomycin and Compound A) to the nonionic adsorption resin and eluting with the silver ion-containing aqueous solvent, the lactone-containing high-molecular weight compounds having a lower alkenyl group as their side-chain could be separated.

Further, the above results show that the lactone-containing high-molecular weight compounds having a lower alkyl group as their side-chain (ascomycin and Compound A) were also separated.

EXAMPLE 3

Separation by column chromatography using, a basic active alumina, AC12

The fractions containing the mixture of tacrolimus and Compound B obtained in Example 2 were concentrated and extracted with ethyl acetate. An organic layer was dried with magnesium sulfate and then evaporated to dryness. The obtained residue was subjected to column chromatography using a basic active alumina, AC 12 (20 mL) packed with ethyl acetate. At room temperature, elution was carried out by using ethyl acetate (400 mL) as an eluent and separate fractions (20 mL×1 and 200 mL×2) were obtained.

The quantity of each compound contained in the separate fractions thus obtained was measured by HPLC analysis in the same manner as in Example 2. The results of separation of tacrolimus and compound B are shown in Table 2.

TABLE 2

| Fraction No. | Liquid amount | Tacrolimus | Compound B |
|---|---|---|---|
| 1 | 20 mL | 0% | 0% |
| 2 | 100 mL | 59.7% | 0% |
| 3 | 100 mL | 10.4% | 0% |
| Total | 220 mL | 70.1% | 0% |

As clearly seen from Table 2, by absorbing the mixture of a lactone-containing high-molecular weight compound having a lower alkoxy group as its side-chain (tacrolimus) and their analogous compound (Compound B) to the basic active alumina and eluting with the organic solvent, the lactone-containing high-molecular weight compound having a lower alkoxy group as its side-chain could be separated.

Further, the above results show that the lactone-containing high-molecular weight compound having a hydroxy group as its side-chain (Compound B) was also be separated.

Tacrolimus, which is a lactone-containing high-molecular weight compound having a lower alkenyl group and a lower alkoxy group as its side-chains, was separated by carrying out Examples 2 and 3, i.e., by carrying out the step of adsorption by the nonionic adsorption resin and elution with the silver ion-containing aqueous solvent and the step of adsorption by the basic active alumina and elution with the organic solvent in this order or in reverse order on the solution containing a mixture of tacrolimus and its analogous compound.

INDUSTRIAL APPLICABILITY

According to the present invention, a lactone-containing high-molecular weight compound having at least one of a lower alkenyl group and a lower alkoxy group as its side-chain(s) can be separated from analogous compound(s) with unexpectedly high efficiency by conducting either one or both steps of a step for adsorbing to a nonionic adsorption resin and eluting with a silver ion-containing aqueous solvent and a step for adsorbing to a basic active alumina and eluting with an organic solvent.

What is claimed is:

1. A method for separating a lactone-containing high-molecular weight compound comprising,
    subjecting a mixture of a lactone-containing high-molecular weight compound having, as its side-chain, at least one of a lower alkenyl group and a tower alkoxy group and its analogous compound(s) to (A) or (A) and (B) in any order,
    (A) adsorbing the mixture to a nonionic adsorption resin and eluting with an aqueous solvent containing silver ions,
    (B) adsorbing the mixture to a basic active alumina and eluting with an organic solvent to separate each of the compounds.

2. A method according to claim 1, wherein the lactone-containing high-molecular weight compound has both a lower alkenyl group and a lower alkoxy group as its side-chains and is separated by conducting the steps (A) and (B) in this order or in reverse order.

3. A method according to claim 2, wherein the lactone-containing high-molecular weight compound has a basic chemical structure of 1,14-dihydroxy-12-[2-(4-hydroxy-cyclohexyl)-1-methylvinyl]-23,25-dimethoxy-13,19,21,27-tetramethyl-11,28-dioxa-4-azatricyclo-[22.3.1.0$^{4,9}$]octacos- 18-ene-2,3,10,16-tetraone, the lower alkenyl group as the side chain is a propenyl group and the lower alkoxy group as the side chain is a methoxy group.

4. A method according to claim 2, wherein the analogous compound is a lactone-containing high-molecular weight compound having, as its side-chains, a lower alkyl group and a hydroxy group instead of the lower alkenyl group and the lower alkoxy group, respectively.

5. A method according to claim 1, wherein the lactone-containing high-molecular weight compound has a lower alkenyl group as its side-chain and is separated by conducting the step (A).

6. A method according to claim 5, wherein the lactone-containing high-molecular weight compound has a basic chemical structure of 1,14-dihydroxy-12-[2-(4-hydroxy-cyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone, and the lower alkenyl group as the side chain is a propenyl group.

7. A method according to claim 5, wherein the analogous compound is a lactone-containing high-molecular weight compound having, as its side-chain, a lower alkyl group instead of the lower alkenyl group.

8. A method according to claim 1, wherein the lactone-containing high-molecular weight compound has a lower alkoxy group as its side-chain and is separated by conducting the step (B).

9. A method according to claim 8, wherein the lactone-containing high-molecular weight compound has a basic chemical structure of 1,14-dihydroxy-12-[2-(4-hydroxy-cyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone, and the lower alkoxy group as the side chain is a methoxy group.

10. A method according to claim 8, wherein the analogous compound is a lactone-containing high-molecular weight compound having, as its side-chain, a hydroxy group instead of the lower alkoxy group.

11. A method according to claim 1, wherein the lactone-containing high-molecular weight compound and its analogous compound(s) are tricyclic compounds.

12. A method according to claim 11, wherein the lactone-containing high-molecular weight compound has a basic chemical structure of 1,14-dihydroxy-12-[2-(4-hydroxy-cyclohexyl)-1-methylvinyl]-23,25-dimethoxy-13,19,21,27-tetramethyl-11,28-dioxa-4-azatncyclo-[22.3.1.0$^{4,9}$]octacos-18-ene-2,3,10,16-tetraone.

13. A method according to claim 1, wherein the nonionic adsorption resin has a partial structure represented by the formula:

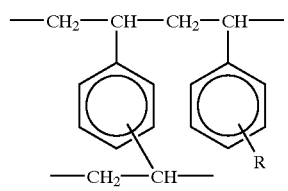

wherein R is a hydrogen atom or a halogen atom.

* * * * *